United States Patent [19]
Tanaka

[11] Patent Number: 5,830,128
[45] Date of Patent: Nov. 3, 1998

[54] LIQUID FEED DEVICE FOR INTRACAVITARY EXAMINATION INSTRUMENT

[75] Inventor: Toshizumi Tanaka, Omiya, Japan

[73] Assignee: Fuji Photo Optical Co., Ltd., Omiya, Japan

[21] Appl. No.: 779,239

[22] Filed: Jan. 3, 1997

[30] Foreign Application Priority Data

Jan. 9, 1996 [JP] Japan .................................. 8-018035

[51] Int. Cl.⁶ ........................................................ A61B 1/12
[52] U.S. Cl. ........................... 600/158; 604/257; 137/433
[58] Field of Search ............................. 600/156, 158, 600/159; 604/30, 31, 33, 246, 257, 258, 259, 260, 254; 222/630; 141/192, 197, 196, 199, 204; 137/202, 433

[56] References Cited

U.S. PATENT DOCUMENTS

| | | | |
|---|---|---|---|
| 3,667,464 | 6/1972 | Alligood, Jr. ......................... | 137/433 X |
| 4,099,527 | 7/1978 | Howell ................................. | 604/257 X |
| 5,297,537 | 3/1994 | Savitt et al. ............................ | 600/158 |
| 5,423,346 | 6/1995 | Daoud ................................. | 137/433 X |

*Primary Examiner*—Beverly M. Flanagan
*Attorney, Agent, or Firm*—Oblon, Spivak, McClelland, Maier & Neustadt, P.C.

[57] ABSTRACT

A liquid feed device for feeding a liquid to an endoscopic or ultrasound insertion instrument or the like from a liquid feeder tank containing a supply of a feed liquid. A liquid feed pipe and an atmospheric pipe which are led into the feeder tank are provided with flexible pipe portions formed of a flexible material of greater specific gravity than the feed liquid in the tank and suspended flexibly within the feeder tank to hang down always in a vertical position by gravity and in such a way as to hold a liquid intake end of the liquid pipe in a deeper position than a pressure discharge opening of the atmospheric pipe relative to the liquid surface even when the feeder tank is turned from an upright position into a tilted position through a certain angle or vice versa.

9 Claims, 6 Drawing Sheets

LIQUID FEED DEVICE FOR INTRACAVITARY EXAMINATION INSTRUMENT

BACKGROUND OF THE INVENTION

1. Field of the Art

This invention relates generally to intracavitary examination instruments such as endoscopes, ultrasound probes or the like, and more particularly to a liquid feed device for sending a liquid such as wash liquid, deaerated water or the like into a body cavity through an intracavitary insertion instrument.

2. Prior Art

Endoscopes and ultrasound probes are typical of intracavitary insertion instruments to be introduced into body cavities for examination or diagnostic purposes. For example, in case of an intracavitary ultrasound examination using an ultrasound insertion instrument, it is a matter of an utmost importance to suppress attenuation of ultrasound signals. In this regard, it has been the usual practice to fit a balloon around an ultrasound transducer on a distal end portion of an ultrasound insertion instrument or to supply deaerated water directly into a body cavity of an examination site for transmission and reception of ultrasound signals through deaerated water.

Figure 7:
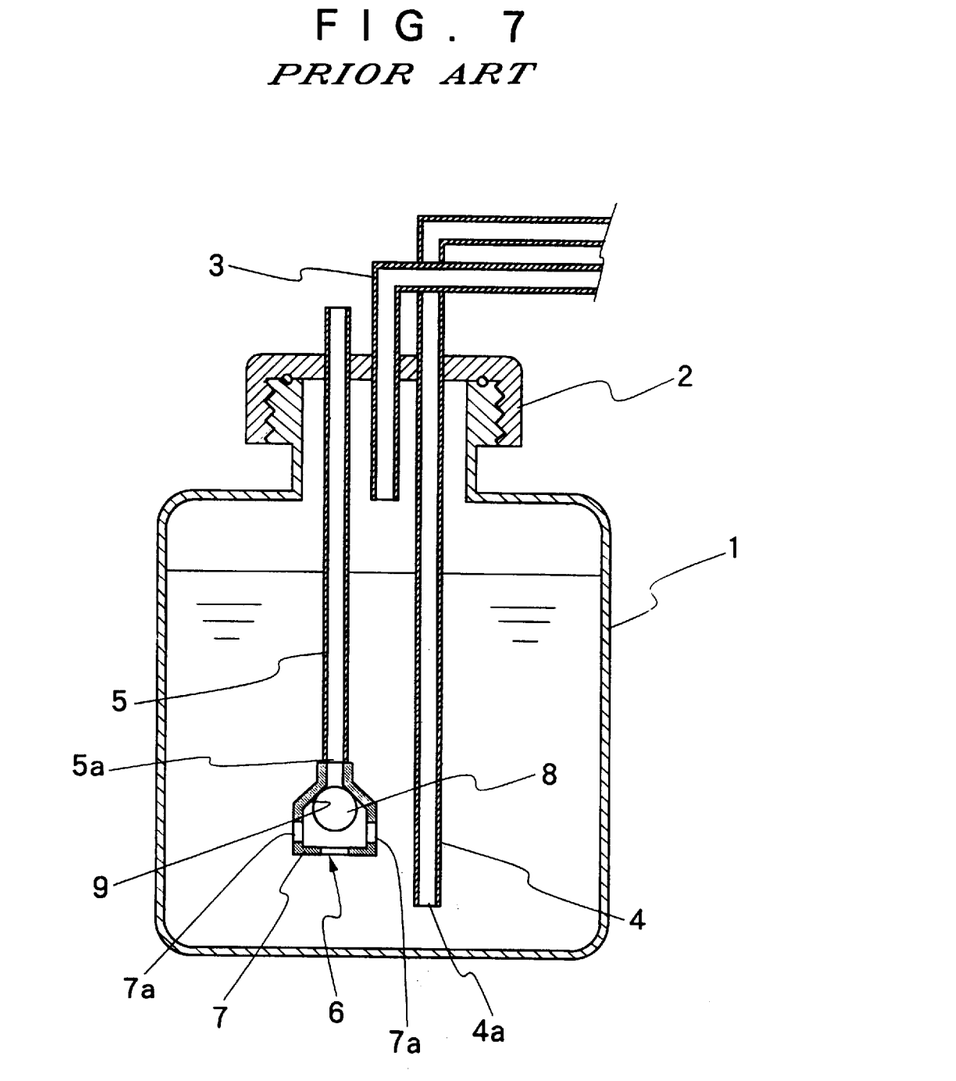
FIG. 7 is a schematic sectional view of a prior art liquid feed device.

Shown in FIG. 7 is a deaerated water feed device by prior art, employing a deaerated water feeder tank 1 which is hermetically closed with a lid 2. A supply of deaerated water is sent out by pressurizing an internal space of the feeder tank 1. For sending deaerated water from the tank 1 to a body cavity, a pressure is applied on a liquid surface in the feeder tank 1. Through the lid 2, one end of a pressurizing pipe 3 is led into the feeder tank 1 and opened above the liquid surface in the tank 1 to introduce pressurized air over the liquid surface by operation of an air pump which is connected to the other end of the pressurizing pipe 3. A liquid supply pipe 4 which is also led into the tank 1 through the lid 2 is dipped in the liquid in the tank 1 to have its lower liquid intake end under the liquid surface. The other end of the liquid pipe 4 is connected to a deaerated water passage in an ultrasound examination instrument. Accordingly, upon introduction of pressurized air, the internal pressure of the tank 1 is elevated to send out deaerated water under pressure through the liquid pipe 4.

As soon as a certain amount of deaerated water is sent out, the liquid surface level in the feeder tank 1 drops below the intake end of the liquid pipe 4 to make further supply of deaerated water impossible. Under these circumstances, if the feeder tank 1 is continuedly held in a pressurized state, there inevitably occurs a situation that pressurized air in the tank 1 flows into the liquid supply passage in the ultrasound insertion instrument through the liquid feed pipe 4. Therefore, in many cases the liquid feeder tank 1 is provided with a mechanism which prevents the liquid surface in the tank 1 from dropping to a level below the intake end 4a of the liquid pipe 4, namely, a depressurizing mechanism which monitors the liquid surface in the tank 1 and releases the pressure of the tank 1 as soon as the liquid surface drops to a predetermined critical level. The depressurizing mechanism of this sort employs, side by side with the liquid pipe 4, an atmospheric pipe 5 which opens to the atmosphere at its outer end and which communicate the pressurizing air space in the tank 1 with the atmosphere for lowering the tank pressure to the atmospheric level whenever the liquid surface drops below a predetermined level.

To this end, the atmospheric pipe 5, which is in communication with the atmosphere at its outer end, is provided with a float valve assembly 6 at its inner end which is opened into the tank 1. The valve assembly 6 has a float valve body 8 accommodated in a valve casing 7 which is bored with a number of communication holes 7a in its peripheral walls. The valve body 8 is constituted by a globular float member of smaller specific gravity than deaerated water in the liquid feeder tank 1. The float valve 8 is seated on a valve seat 9 on the valve casing 8 to close the inner open end 5a of the atmospheric pipe 5 when the liquid surface in the tank 1 is at a higher level than the inner end 5a of the atmospheric pipe 5. As soon as the liquid surface drops below the inner open end 5a of the atmospheric pipe 5, the valve body 8 is unseated away from the valve seat 9 to open the lower end of the of the atmospheric pipe 5, namely, to communicate the tank 1 with the atmosphere through the atmospheric pipe 5. Accordingly, by way of the atmospheric pipe 5 which has its inner open end 5a at a higher level than the liquid feed pipe 4 within the tank 1, the internal pressure of the tank 1 is lowered to the atmospheric pressure by releasing pressurized air into the atmosphere upon a fall of the liquid surface level below the inner open end of the atmospheric pipe 5, prohibiting further supply of deaerated water. Consequently, the liquid surface level in the tank 1 is prevented from dropping below the lower intake end 4a of the liquid pipe 4 to preclude the possibilities of intrusion of pressurized air into the liquid feed pipe 4.

In this connection, considering that the liquid surface level in the feeder tank would not drop below the intake end of the liquid feed pipe 4, it becomes possible to feed a larger amount of liquid by using a feeder tank of a narrower and taller shape instead of a tank which is equivalent in volume but wider and shorter in shape. However, since it is often the case that a feeder tank is in the form of a plastic container with relatively thin walls, tall tanks involve the problem of deformations under pressure, more specifically, are likely to bulge out in upper portions when the liquid level drops to a certain degree under pressurized condition. In deformed state, a tall tank becomes instable and could easily fall down flat during use. In some cases, one might like to put a tank of this sort on a rack or shelf instead of on a floor surface. However, naturally a rack or shelf has limits in capacity, particularly in height, and may not be able to hold a tall tank in an upright position.

If a tall tank is inclined or tilted in use or when a tank happens to fall down flat during use, the positional relationship between the float valve assembly at the inner end of the atmospheric pipe and the intake end of the liquid feed pipe is reversed relative to the liquid surface in the tank, and the intake end of the liquid feed pipe is turned into a shallower position closer to the liquid surface. In such reversed positions, the atmospheric pipe would not communicate with the atmosphere even when the intake end of the liquid feed pipe were exposed over the liquid surface to bring about a perilous situation that pressurized air suddenly flows into a body cavity through the liquid feed pipe during a liquid feed.

SUMMARY OF THE INVENTION

It is an object of the present invention to provide a liquid feed device for an intracavitary examination instrument, which can maintain an inner pressure discharge end of an atmospheric pipe constantly in a shallower position than an intake end of a liquid feed pipe relative to a liquid surface within a feeder tank even if the tank is leaned or turned into a tilted position or posture while in use.

It is another object of the present invention to provide a liquid feed device of the sort as mentioned above, employing a liquid feeder tank which can securely preclude accidental intrusion of pressurized air into a body cavity while feeding a liquid thereto from the tank through an inserted intracavitary examination instrument.

It is still another object of the present invention to provide a liquid feed device of the sort as mentioned above, which has greater freedom with regard to the posture of a liquid feeder tank in use.

In accordance with the present invention, the above-stated objectives are achieved by the provision of a liquid feed device for an intracavitary insertion instrument, comprising a hermetically closed liquid feeder tank containing a supply of a feed liquid, a liquid feed pipe hermetically led into the feeder tank and having a liquid intake end thereof dipped in the feed liquid in the feeder tank to supply the liquid to a liquid supply passage in an intracavitary insertion instrument, a pressurizing pipe hermetically led into the feeder tank and having a pressure delivering end thereof opened over a liquid surface in the tank to apply pressure thereon, an atmospheric pipe having one end thereof hermetically led into and opened in the liquid feeder tank and having the other end communicated with the atmosphere, and a valve assembly mounted on a pressure discharge opening at a lower distal end of the atmospheric pipe to keep same closed while in a submerged position under the liquid surface in the feeder tank and to uncover the opening when brought into an exposed position above the liquid surface in the feeder tank, the above-mentioned liquid feed pipe and atmospheric pipe being formed of a flexible material having greater specific gravity than the feed liquid in the tank and flexibly supported within the feeder tank to hang down always in a vertical state by gravity and in such a way as to hold the intake end of the liquid pipe in a deeper position than the pressure discharge opening of the atmospheric pipe relative to the liquid surface even when the feeder tank is turned from an upright position into a tilted position through a certain angle or vice versa.

BRIEF DESCRIPTION OF THE DRAWINGS

The above and other objects, features and advantages of the invention will become apparent from the following description, taken in conjunction with the accompanying drawings which show by way of example preferred embodiments of the invention and in which.

DESCRIPTION OF PREFERRED EMBODIMENTS

The liquid feed device of present invention, which will be described hereinbelow, can find various applications, for example, in ultrasound examination instruments to serve as a deaerated water feed device which supplies deaerated water to a body cavity through an ultrasound insertion instrument, or in endoscopic examination instruments to serve as a wash liquid feed device which supplies a wash liquid to a distal end of an endoscope for washing an endoscopic observation window or for washing intracavitary walls under observation.

Figure 1:
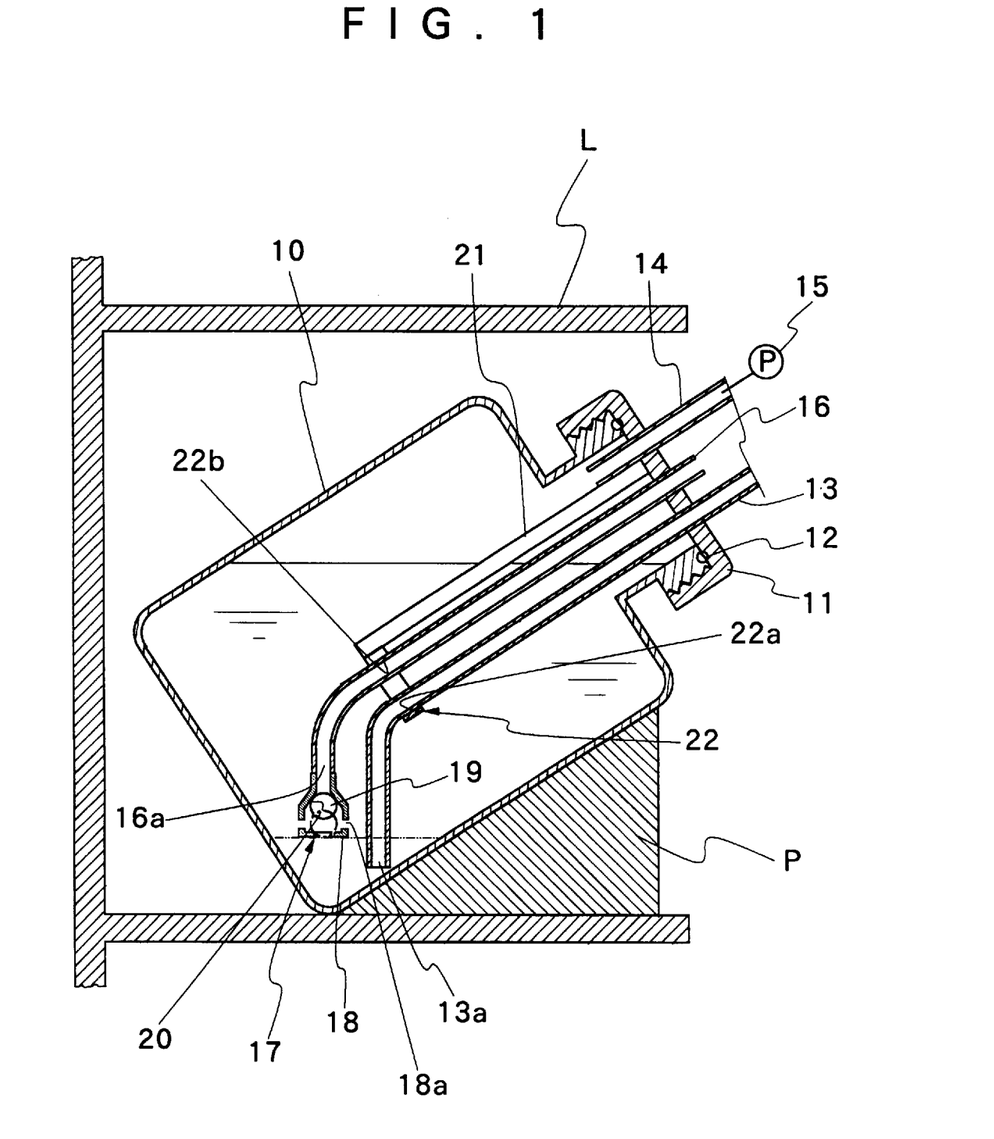
FIG. 1 is a schematic sectional view of a liquid feed device according to the invention.

Referring first to FIG. 1, indicated at 10 is a liquid feeder tank 10 which is filled with a supply of feed liquid like deaerated water and which is hermetically closed with a lid 11. Indicated at 12 is a seal member 12 which is interposed between the tank 10 and the lid 11. Although the tank 10 can be set in an upright position by itself while in use, it may be used in a tilted state with the tank body inclined through a certain angle in an arbitrary direction. For example, the tank 10 can be placed in a tilted state on an inclined bed plate P of a rack L in such a way that the tank body is inclined downward gradually toward its bottom end from its top end with the lid 11 as shown particularly in FIG. 1. Led into the feeder tank 10 are three pipes which are hermetically connected to and passed through the lid 11.

The first one of the just-mentioned three pipes is a liquid feed pipe 13 having an open liquid intake end 13a led into the feeder tank 10 through the lid 11 and dipped in the feed liquid in the tank 10. The other end of the feed liquid pipe 13 is detachably connectible to a liquid supply passage in an ultrasound or endoscopic insertion instrument. The open intake end 13a of the liquid pipe 13 is extended to as low as a position which is always submerged under the liquid surface in the feeder tank 10 to take in the feed liquid as much as possible.

The second one of the above-mentioned three pipes is an pressurizing pipe 14 which has one end thereof led into and opened in the feeder tank 10 under the surface of the feed liquid in the tank 10. The other end of the pressurizing pipe 14 is connected to an air pump 15 or other pressure source. Accordingly, a liquid feed pressure is applied on the liquid surface in the feeder tank 10 by introducing pressurized air into a pressurizing space over the feed liquid surface.

The last one of the three pipes is an atmospheric pipe 16 which has one end thereof led into and opened in the feeder tank 10 to prevent the liquid surface level in the tank 10 from dropping below the intake end of the liquid feed pipe 13 by discharging pressurized air in the tank 10 to the atmosphere. Accordingly, the atmospheric pipe 16 has a function of detecting the liquid surface level in the feeder tank 10, along with a function of discharging the air pressure in the tank 10 to the atmosphere when the liquid surface drops to a predetermined level. For these purposes, the atmospheric pipe 16 is provided with a valve assembly 17 at its inner end and communicated with the atmosphere at its outer end which is led out through the lid 11.

The valve assembly 17 includes a valve casing 18 which is formed in such a way as to circumvent a pressure discharge opening 16a at the inner end of the atmospheric pipe 16 and provided with a plural number of communication holes 18a at least in its circumferential walls. Accommodated in the valve casing 18 is a globular float valve member 19 which is smaller in specific gravity than deaerated water or feed liquid in the feeder tank 10. Depending upon the liquid surface level in the feeder tank 10, the float valve member 19 is seated and unseated on and off a valve seat 20 which is formed around the pressure discharge opening 16a at the inner end of the atmospheric pipe 16. In this instance, the valve casing 18 serves as a retainer or holder for the float valve member 19, which therefore has a greater diameter than the communication holes 18a in the valve casing 18. If desired, the valve casing 18 may be formed in other shapes, for example, in the shape of a cage or the like as long as it can hold the valve body 19 therein while permitting inward and outward liquid flows to seat and unseat the valve member 19 relative to the valve seat 20. In this regard, the float valve member 19 has a body of such weight and shape as will ensure large buoyancy in deaerated water or other feed liquid but will not practically impart any buoyancy in air despite a pressure differential between introduced air pressure in the tank 10 and the atmospheric pressure.

While the valve assembly 17 at the inner end of the atmospheric pipe 16 is under the liquid surface, the valve member 19 is seated on the valve seat 20 by its buoyancy to keep the atmospheric pipe 16 in closed state as indicated by solid line in FIG. 1. Should the liquid surface level drop below the valve assembly 17 as indicated by imaginary line in the same figure, the valve member 19 loses its buoyancy and comes off the valve seat 20 by gravity. As a result, the pressurizing space in the tank 10 is communicated with the atmosphere through the atmospheric pipe 19 to release the air pressure out of the tank 10, depressurizing the feeder tank 10 to stop a liquid feed through the pipe 13.

According to the invention, no matter whether the feeder tank 10 is placed in an upright position or in a tilted position as shown in FIG. 1, the valve assembly 17 at the lower end of the atmospheric pipe 16 and the intake end 13a of the liquid feed pipe 13 are maintained in the same positional relations relative to the liquid surface in the tank 10. Namely, irrespective of the posture of the tank 10, the valve assembly 17 is always retained in a shallower position than the intake end 13a of the liquid pipe 13 relative to the liquid surface in the tank 10.

More specifically, the atmospheric pipe 16 and the liquid feed pipe 13 are each arranged to hang down within the feeder tank 10 substantially vertically in a rectilinear form at least over a predetermined length from the lower end of the pipe irrespective of the posture of the tank 10 which may be in an upright position or in an inclined tilted position. For this purpose, the atmospheric pipe 16 and the liquid feed pipe 13 are provided with flexible pipe portions in the respective lower end portions, the flexible pipe portions formed of a material having greater specific gravity than the feed liquid in the feeder tank 10 so that they can flex into a vertical position automatically by gravity irrespective of the posture of the feeder tank 10 in use. With regard to the atmospheric pipe 16 with the valve assembly 17 at its lower end, the just-mentioned requirement can be met if its specific gravity as a whole including the valve assembly 17 is greater than that of the feed liquid. Particularly, by employing a valve casing of a relatively heavy weight for the valve assembly 17, the atmospheric pipe 16 can be invariably maintained in a vertical position by gravity irrespective of the specific gravity of the material of the atmospheric pipe 16 itself.

Besides, arrangements should be made such that the valve seat 20 on the atmospheric pipe 16 is always located in a shallower position than the intake end 13a of the liquid feed pipe 13 relative to the liquid surface even if the tank 10 is in a tilted state. For instance, the liquid pipe 13 and atmospheric pipe 16 may be positioned parallel with each other so that the intake end of the liquid pipe 13 is invariably located in a lower position when the liquid feeder tank 10 is in an upright position and as long as the tank 10 is tilted in certain predetermined directions.

Figure 2:
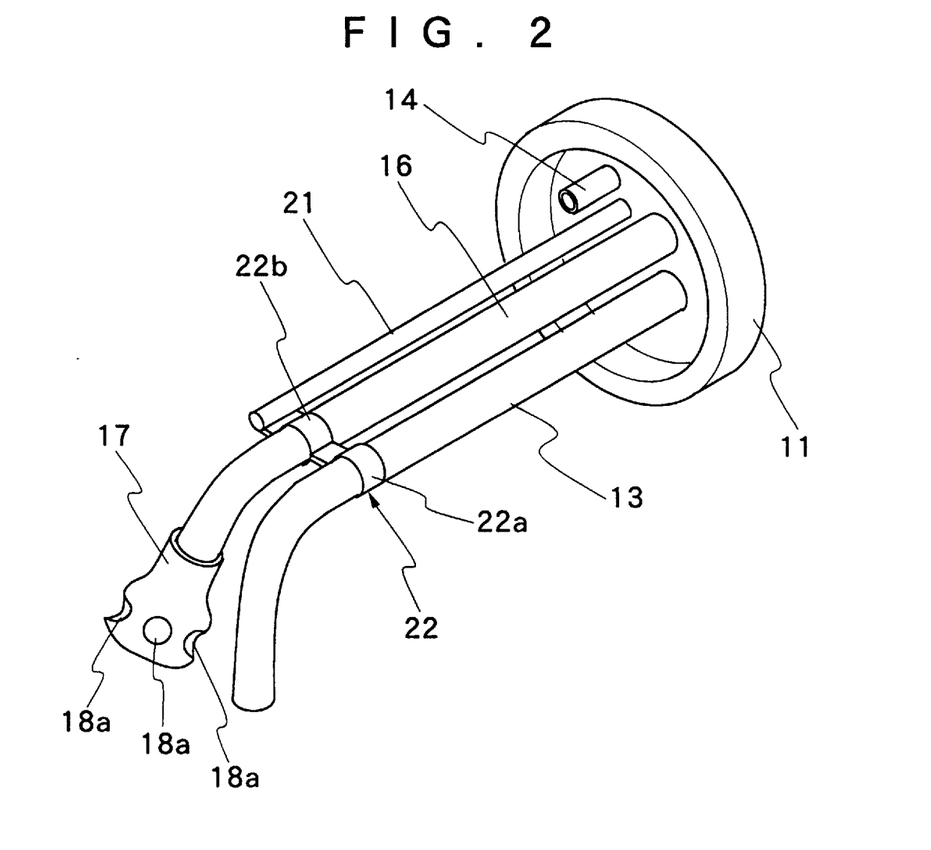
FIG. 2 is a perspective view of a pipe and lid assembly with a brace member for holding a liquid feed pipe and an atmospheric pipe in parallelly spaced positions.

If desired, arrangements can also be made such that the valve seat 20 on the atmospheric pipe 16 is always located in a shallower position than the intake end 13a of the liquid feed pipe 13 irrespective of tilting directions of the tank 10. For this purpose, as shown in FIGS. 1 and 2, one or a plural number of rigid support arms 21 are hung down from the inner or lower side of the lid 11. Fixedly mounted on a fore or lower end portion of the support arms 21 is a brace member 22 which is provided with clamp portions 22a and 22b for securely holding the liquid feed pipe 13 and the atmospheric pipe 16, respectively, which are flexible at least in fore or lower end portions which are suspended from the brace member 22. Of course, each one of the liquid feed pipe 13 and atmospheric pipe 16, which are fixed relative to the support arm 21, may be provided with a flexible body over its entire length and allowed to bend freely in a lower end portion which hangs down from the brace member 22. Considering the hermetic tightness of the feeder tank 10, it is desirable for the liquid feed pipe 13 and the atmospheric pipe 16 to be formed of a rigid pipe at least in an upper portion which is connected to the lid 11.

The liquid feed pipe 13 is longer than the atmospheric pipe 16 in terms of the lengths of the respective lower end portions hanging down from the brace member 22, by a measure which is greater than the width of spacing between the liquid feed pipe 13 and the atmospheric pipe 16. By so arranging, as shown in FIG. 1, the lower intake end 13a of the liquid feed pipe 13 is all the time located in a deeper position than the valve seat 20 on the atmospheric pipe 16 no matter whether the feed liquid feeder tank 10 is plated on a rack L in a tilted state as shown in FIG. 1 or no matter whether the tank 10 is tilted in any direction. Accordingly, before the liquid surface level in the tank 10 drops below the intake end 13a of the liquid feed pipe 13, the pressurizing space in the tank 10 is invariably communicated with the atmosphere to discharge pressurized air, completely precluding the possibilities of intrusion of pressurized air into a body cavity through the liquid feed pipe 13.

With the arrangements as described above, upon actuating the pump 15 to send pressurized air into the pressurizing air space in the feeder tank 10, the feed liquid is pushed into the liquid pipe 13 by pressurization of the liquid surface and into a deaerated water supply passage of an ultrasound insertion instrument or into a liquid supply passage of an endoscopic insertion instrument which is connected to the other end of the liquid pipe 13. As the liquid is sent out, naturally the liquid surface level in the tank 10 drops. The liquid surface level is allowed to drop as low as the level of the valve assembly 17 at the lower end of the atmospheric pipe 16, where the valve member 19 loses buoyancy and disengages from the valve seat 20 by gravity. Whereupon, the pressurizing air space of the tank 10 is communicated with the atmosphere through the atmospheric pipe 16 to depressurize the tank 10 to the atmospheric level. As a result, the feeder tank 10 loses a liquid feed pressure and stops liquid supply through the pipe 13.

Thus, except for a situation where the feeder tank 10 is turned upside down, flexible portions of the liquid pipe 13 and atmospheric pipe 16 are each maintained in a vertical position relative to the liquid surface not only when the tank 10 is in an upright position but also when the tank 10 is tilted through an arbitrary angle. Besides, the liquid pipe 13 is arranged in such a length that its intake end 13a always takes a deeper position than the atmospheric pipe 16 under the liquid surface, so that there is no possibility of the liquid surface level dropping below the intake end 13a of the liquid pipe 13 and letting pressurized air flow into a body cavity through the liquid pipe 13. Namely, the atmospheric pipe 16 which limits falling of the liquid surface level in the feeder tank 10 is located invariably at a higher level than the intake end 13a of the liquid pipe 13 all the time. In addition, in case the lower ends of the atmospheric pipe 16 and liquid pipe 13 are oriented to flex toward one corner portion of the tank 10 where the feed liquid gathers when tilted, it becomes possible to send out the feed liquid in an amount almost corresponding to the full capacity of the tank 10 and to reduce the frequency of refilling the tank 10.

Figure 3:
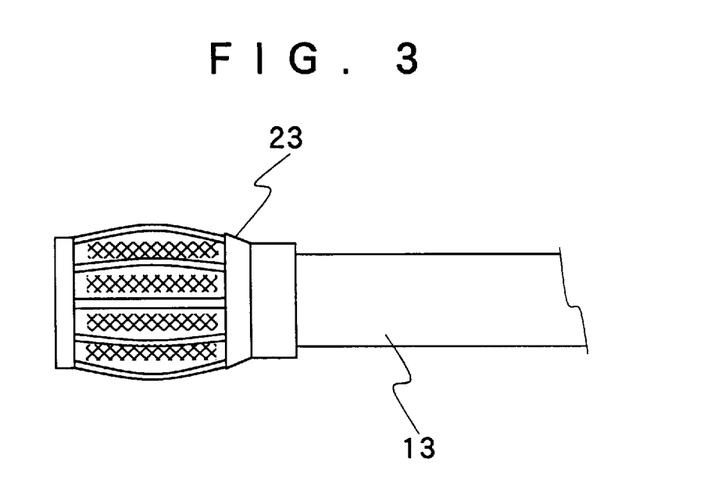
FIG. 3 is a schematic fragmentary view of the liquid feed pipe with a spacer enclosure fitted on its liquid intake end.

In case the feeder tank 10 is allowed to tilt through an arbitrary angle in any arbitrary direction, the lower intake end 13a of the liquid pipe 13 may come into abutting engagement with an inner surface of the feeder tank 10 depending upon the degree of tilting. On such an occasion, the opening of the intake end 13 could be blocked by intimate engagement with an inner surface of the tank 10 to such a degree as to infeasibilize further liquid feed. In order to avoid this, for example, a cage-like spacer enclosure 23 may be fitted around the lower intake end of the liquid pipe 13 as shown in FIG. 3 so that the latter can take in the feed liquid from any direction as long as it is in a submerged state. The spacer enclosure is preferred to be of a relatively heavy weight for positively keeping the liquid pipe 13 in a vertically pendant position in the flexible pipe portion which hangs down from the brace member 22.

Figure 4:
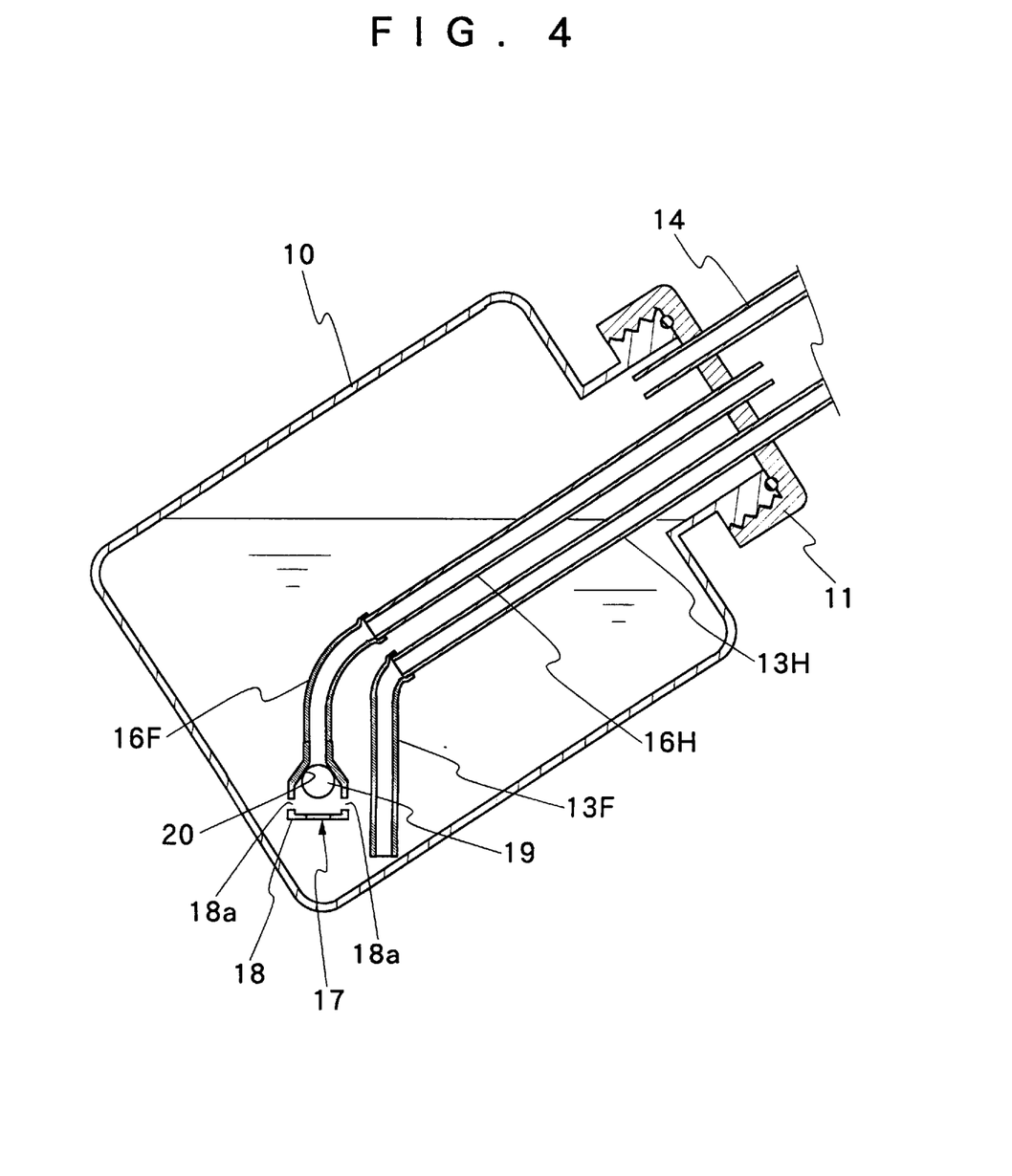
FIG. 4 is a view similar to FIG. 1 but of another embodiment of the invention, showing an example of modified liquid and atmospheric pipes.

In place of the brace member 22 and support arm 21 which are employed in the foregoing embodiment, the liquid pipe 13 and atmospheric pipe 16 may be maintained in vertical positions by other means, for example, by providing rigid pipe portions as in another embodiment shown in FIG. 4.

More specifically, in the embodiment of FIG. 4, the liquid feed pipe and atmospheric pipe are constituted by rigid or hard pipe sections 13H and 16H and flexible pipe sections 13F and 16F, respectively. The rigid pipe sections 13H and 16H are hermetically passed through the lid 11 and extended downwardly into the liquid feeder tank 10 beyond an intermediate position between the top and bottom sides of the tank 10. Connected to the lower ends of these rigid pipe sections 13H and 16H are flexible pipe sections 13F and 16F, respectively. A valve assembly 17 is mounted on the lower distal end of the flexible pipe section 13H of the liquid pipe 13 in the same manner as in the foregoing embodiment. If necessary, a spacer enclosure 23 may be likewise fitted on the lower intake end of the flexible pipe section 13F of the liquid feed pipe 13. Similarly, the lower flexible pipe section 16F of the atmospheric pipe 16, including the valve assembly 17, and the lower flexible pipe section 13F of the liquid pipe 13, including a spacer cage if any, are both arranged to have greater specific gravity than a feed liquid in the feeder tank 10.

In order to permit tilting of the feeder tank 10 with the pipe arrangements Just-described, dimensional relations in length between the flexible pipe sections 13F and 16F of the liquid pipe 13 and atmospheric pipes 16 should be determined such that the lower end of the flexible pipe section 13F always takes a deeper position than the lower end of the flexible pipe section 16F irrespective of the posture of the feeder tank 10 in use. In case the rigid pipe sections 13H and 16H within the tank 10 have same lengths, the lower ends of the two pipes can be maintained in the required positional relations by arranging the flexible pipe section 13F of the liquid pipe 13 in a length greater than the flexible pipe section 16F of the atmospheric pipe 16 at least by a length corresponding to an interval or a spacing between the two pipes. However, the rigid pipe sections 13H and 16H are not necessarily required to be same in length.

Figure 5:
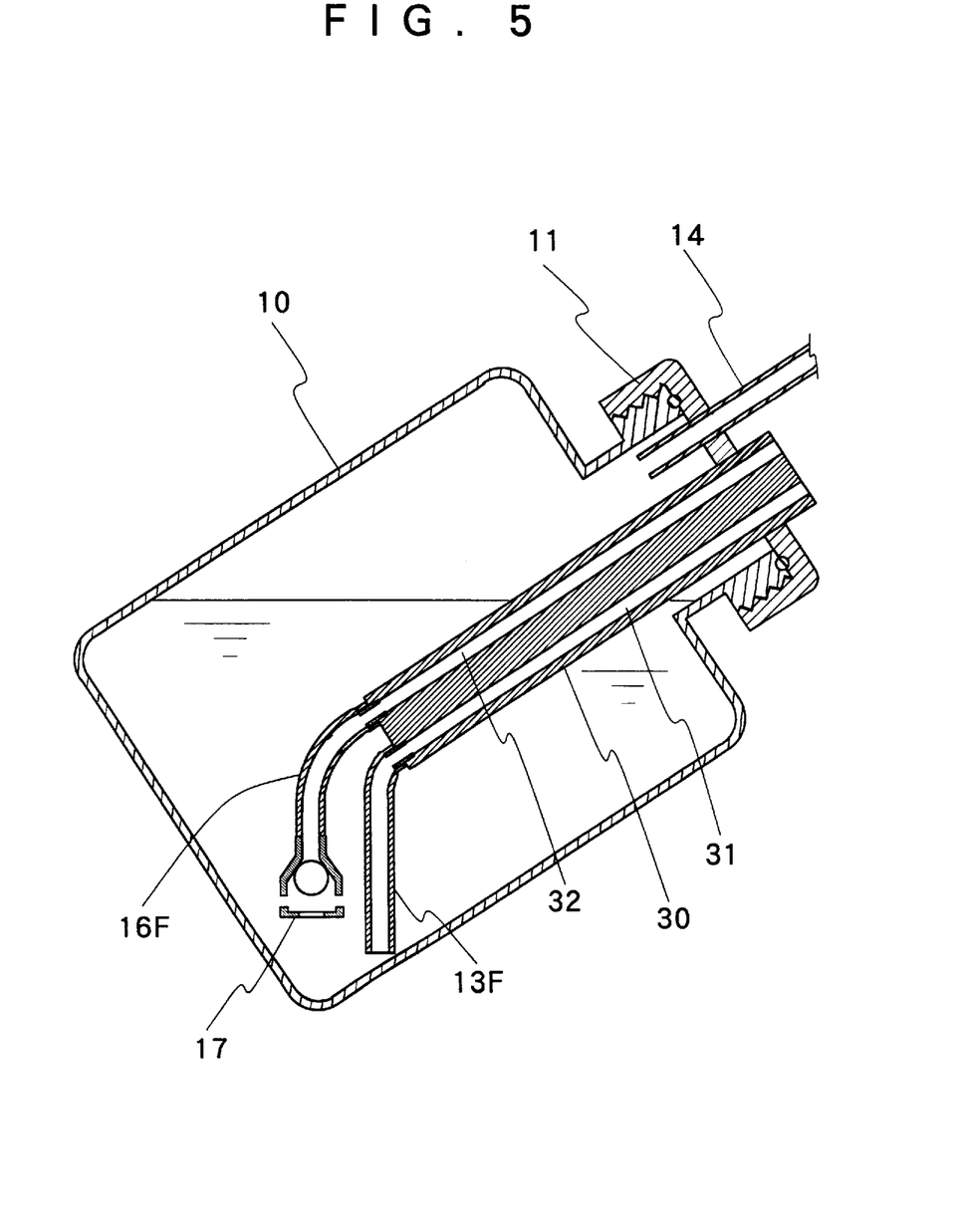
FIG. 5 is a view similar to FIG. 1 but of still another embodiment of the invention, showing another example of modified liquid and atmospheric pipes.

Alternatively, as shown particularly in FIG. 5, rigid sections of the liquid pipe 13 and atmospheric pipe 16 may be integrated into a single compound pipe structure 30 having two parallel fluid passages, that is, a liquid feed passage 31 and an atmospheric passage 32. A flexible liquid feed pipe 13F and a flexible atmospheric pipe 16F are connected to the lower end of the rigid pipe 30 in communication with the liquid feed passage 31 and atmospheric passage 32, respectively. Similarly to the foregoing embodiments, the flexible liquid feed pipe 13F and the flexible atmospheric pipe 16F are provided with a valve assembly 17 and a spacer enclosure 23 at their lower ends, respectively. In this case, simply a longer flexible tube is used for the liquid feed pipe 13F.

Figure 6:
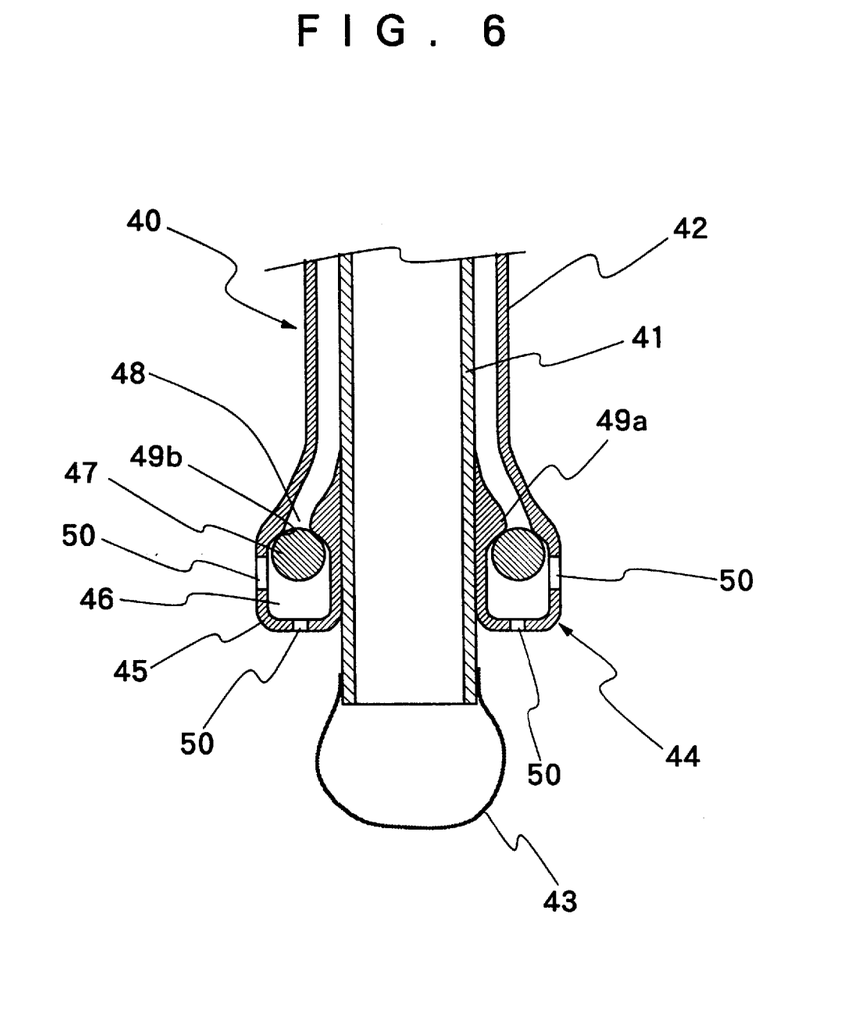
FIG. 6 is a view similar to FIG. 1 but of a further embodiment of the invention, showing a further example of modified liquid and atmospheric pipes.

Alternatively, a double tube 40 having an inner tube 41 and an annular outer tube 42 may be employed for the liquid feed pipe and the atmospheric pipe as shown in FIG. 6. In this case, the inner tube 41 is used as the liquid feed pipe and the outer tube 42 as the atmospheric pipe. The inner tube 41 is extended further downward of the outer tube 42 and terminated with an open liquid intake end 41a. A wire net enclosure 43 is fitted around the liquid intake end 41a as a spacer to prevent same from being blocked when abutted against an inner surface of the tank 10 as described hereinbefore. Besides, except for upper portions on the side of the lid 11, the double tube 40 is formed of a flexible material so that its lower portions can flex in any direction to maintain a vertical position within the tank 10.

An annular float valve assembly 44 is mounted on the lower end of the outer tube 42, which is located in a higher position than the liquid intake end 41a of the inner tube 41. The valve assembly 44 is provided with a valve casing 45 which is of an annular shape around the inner tube 41 similarly to the outer tube 42 which surrounds the inner tube 41. Formed internally of the valve casing 45 is an annular valve chamber 46 which accommodates therein a ring-like float valve body 47. Opened into the valve casing 45 is an annular passage 48 of the outer tube 42, which is communicated with the valve chamber 46 through annular valve seats 49b and 49b. The inner valve seat 49a is larger than the inner diameter of the valve body 47, while the outer valve seat 49b is smaller than the outer diameter of the valve body 47. Further, the valve casing 45 is bored with a plural number of communication holes 50 in suitably spaced positions on its outer peripheral walls and bottom walls.

With the arrangements just described, similarly to the foregoing embodiments, the lower intake end 41a of the inner tube 41 is always located in a deeper position than the valve assembly 44 at the lower end of the outer tube 42 under the liquid surface of the feeder tank 10 even if the tank 10 is tilted in an arbitrary direction during a liquid feeding operation.

What is claimed is:

1. A liquid feed device for an endoscopic insertion instrument or the like, said liquid feed device comprising:

a hermetically closed liquid feeder tank containing a supply of a feed liquid;

a liquid feed pipe hermetically led into said feeder tank and having a liquid intake end thereof dipped in said feed liquid in said tank to supply said liquid to a liquid supply passage in an intracavitary insertion instrument;

a pressurizing pipe hermetically led into said liquid feeder tank and having a pressure delivering end thereof opened over a liquid surface in said tank to apply pressure thereon;

an atmospheric pipe having one end thereof hermetically led and opened into said liquid feeder tank and having the other end disposed outside said liquid feeder tank in communication with the atmosphere; and a valve assembly mounted on a pressure discharge opening at a lower distal end of said atmospheric pipe within said feeder tank to keep same closed while in a submerged position under the liquid surface in said feeder tank and to uncover said pressure discharge opening when brought into an exposed position above said liquid surface in said feeder tank;

said liquid feed pipe and atmospheric pipe having flexible pipe portions formed of a flexible material of greater specific gravity than said feed liquid in said tank and suspended flexibly within said feeder tank to hang down always in a vertical position by gravity and in such a way as to hold the intake end of said liquid pipe in a deeper position than said pressure discharge opening of said atmospheric pipe relative to said liquid surface even when said feeder tank is turned from an upright position into a tilted position through a certain angle or vice versa.

2. A liquid feed device as defined in claim 1, wherein said liquid feed pipe and said atmospheric pipe are provided with flexible pipe portions of such lengths as to hold said liquid intake end of said liquid pipe always at a deeper position than said pressure discharge opening of said atmospheric pipe under the liquid surface in said feeder tank when said tank is tilted in an arbitrary direction.

3. A liquid feed device as defined in claim 1, wherein said liquid pipe and said atmospheric pipe are supported in parallelly spaced vertical positions by a brace member and provided with flexible pipe portions hanging down from said brace member.

4. A liquid feed device as defined in claim 3, wherein said lower intake end of said liquid pipe is extended further downward of said valve assembly at the lower end of said atmospheric pipe by a distance greater than a spacing between said liquid and atmospheric pipes.

5. A liquid feed device as defined in claim 1, wherein said liquid pipe and said atmospheric pipe within said liquid feeder tank are each constituted by a rigid pipe section and a flexible pipe section connected to the lower end of said rigid pipe section.

6. A liquid feed device as defined in claim 5, wherein said flexible pipe section of said liquid pipe is extended further downward of said valve assembly at the lower end of said flexible pipe section of said atmospheric pipe by a distance greater than a spacing between said liquid pipe and said atmospheric pipe.

7. A liquid feed device as defined in claim 5, wherein said rigid pipe sections of said liquid pipe and atmospheric pipe are integrated into a compound pipe structure with a pair of fluid passages.

8. A liquid feed device as defined in claim 1, wherein said liquid and atmospheric pipes are constituted by a double tube being flexible at least in lower end portions thereof and internally defining an inner core tube and an annular outer tube for said liquid and atmospheric pipes, respectively, and said valve assembly is provided with an annular valve member to open and close an annular pressure discharge opening at the lower end of said outer annular tube at a higher position than a lower liquid intake end of said inner tube.

9. A liquid feed device as defined in claim 1, further comprising a spacer enclosure fitted around said lower intake end of said liquid pipe to prevent same from being blocked when contacted with an inner surface of said feeder tank.

* * * * *